United States Patent
Yang et al.

(10) Patent No.: US 10,933,256 B2
(45) Date of Patent: Mar. 2, 2021

(54) MULTI-LEAF COLLIMATOR AND RADIOTHERAPY DEVICE

(71) Applicants: SHENZHEN OUR NEW MEDICAL TECHNOLOGIES DEVELOPMENT CO., LTD., Guangdong (CN); OUR UNITED CORPORATION, Shaanxi (CN)

(72) Inventors: Bin Yang, Guangdong (CN); Mengmeng Zhang, Guangdong (CN)

(73) Assignees: SHENZHEN OUR NEW MEDICAL TECHNOLOGIES DEVELOPMENT CO., LTD.; OUR UNITED CORPORATION

( * ) Notice: Subject to any disclaimer, the term of this patent is extended or adjusted under 35 U.S.C. 154(b) by 0 days.

(21) Appl. No.: 16/579,125

(22) Filed: Sep. 23, 2019

(65) Prior Publication Data
US 2020/0016430 A1 Jan. 16, 2020

Related U.S. Application Data

(63) Continuation of application No. PCT/CN2017/077487, filed on Mar. 21, 2017.

(51) Int. Cl.
*A61N 5/10* (2006.01)
*G21K 1/04* (2006.01)

(52) U.S. Cl.
CPC .......... *A61N 5/1045* (2013.01); *G21K 1/046* (2013.01)

(58) Field of Classification Search
CPC ........ A61N 5/1045; G21K 1/046; G21K 1/02; G21K 1/025
(Continued)

(56) References Cited

U.S. PATENT DOCUMENTS

| 7,785,098 B1 * | 8/2010 | Appleby ............... G21K 1/02 425/470 |
| 2011/0049396 A1 | 3/2011 | Furth et al. ............... 250/505.1 |

(Continued)

FOREIGN PATENT DOCUMENTS

| CN | 2523447 Y | 12/2002 |
| CN | 101364453 A | 2/2009 |

(Continued)

OTHER PUBLICATIONS

International Search Report dated Dec. 25, 2017 in corresponding PCT International Application No. PCT/CN2017/077487.
(Continued)

*Primary Examiner* — David A Vanore
(74) *Attorney, Agent, or Firm* — Ostrolenk Faber LLP (57) ABSTRACT

A multi-leaf collimator includes two leaf sets disposed opposite to each other, a plurality of drive devices, a U-shaped optoelectronic switching system, and a first processor. Each leaf set includes a plurality of leaves; each leaf is configured to move under driving of the corresponding drive device; one or more U-shaped optoelectronic switches in the U-shaped optoelectronic switching system are disposed at a side of the upper end surface and/or a side of the lower end surface of a leaf; the U-shaped optoelectronic switch includes a U-shaped groove, a transmitter and a receiver; the U-shaped optoelectronic switch system generates pulse signals when the leaf is configured to move in the U-shaped groove; the first processor is configured to process pulse signals output by the U-shaped optoelectronic switch system to obtain a quantized value of the state of motion of a leaf.

15 Claims, 4 Drawing Sheets

(58) Field of Classification Search
USPC .......................................... 250/505.1; 378/147
See application file for complete search history.

(56) References Cited

U.S. PATENT DOCUMENTS

2011/0189440 A1* 8/2011 Appleby .............. B29C 33/301
428/156
2019/0054316 A1* 2/2019 Sheng .................. A61N 5/1045

FOREIGN PATENT DOCUMENTS

| CN | 203874296 U | 10/2014 |
|---|---|---|
| CN | 104147712 A | 11/2014 |
| CN | 204034060 U | 12/2014 |
| CN | 205145419 U | 4/2016 |
| CN | 106017331 A | 10/2016 |
| KR | 10-1674529 B1 | 11/2016 |
| WO | WO 2009/129816 A1 | 10/2009 |

OTHER PUBLICATIONS

Written Opinion dated Dec. 25, 2017 in corresponding PCT International Application No. PCT/CN2017/077487.

* cited by examiner

MULTI-LEAF COLLIMATOR AND RADIOTHERAPY DEVICE

RELATED APPLICATIONS

This application is a Bypass Continuation Application of PCT/CN2017/077487 filed on Mar. 21, 2017, which is incorporated herein by reference in its entirety.

TECHNICAL HELD

The present disclosure relates to the field of medical instruments, more specifically, to a multi-leaf collimator and a radiotherapy device.

BACKGROUND

In one aspect, a multi-leaf collimator is provided, which includes two leaf sets disposed opposite to each other, a plurality of drive devices, a U-shaped optoelectronic switching system, and a first processor. Each leaf set includes a plurality of leaves; each of the leaves includes an upper end surface and a lower end surface opposite to each other, and a front end surface and a rear end surface opposite to each other; the front end surfaces of the leaves in the two leaf sets are facing each other. Each of the leaves is connected to a corresponding drive device, and each of the leaves is configured to move along the facing direction of the two leaf sets under driving of the corresponding drive device. The U-shaped optoelectronic switching system includes one or more U-shaped optoelectronic switches, corresponding to each leaf, arranged in the motion direction of the leaf; the one or more U-shaped optoelectronic switch are disposed at a side of the upper end surface and/or a side of the lower end surface of a corresponding leaf; each U-shaped optoelectronic switch includes a U-shaped groove, a transmitter located at a side of the U-shaped groove and a receiver located at the other opposite side of the U-shaped groove; the corresponding leaf is disposed in the U-shaped groove, when the corresponding leaf is configured to move in the U-shaped groove along the facing direction of the two leaf sets, the U-shaped optoelectronic switch system generates pulse signals. The first processor is connected to the U-shaped optoelectronic switch system and configured to process pulse signals output by the U-shaped optoelectronic switch system to obtain a quantized value of the state of motion of each leaf.

In some embodiments, the upper end surface and/or the lower end surface of the leaf is provided with a trigger structure; the trigger structure is located in the U-shaped groove and is configured to move with the corresponding leaf in the U-shaped groove.

In some embodiments, a width of the trigger structure is less than a width of the corresponding leaf.

In some embodiments, the trigger structure includes a plurality of bosses spaced from each other.

In some embodiments, a width of the boss and/or a distance between two adjacent bosses is equal to a width of the U-shaped optoelectronic switch.

In some embodiments, a plurality of the U-shaped optoelectronic switches corresponding to each leaf are sequentially arranged adjacent to each other or spaced from each other.

In some embodiments, the multi-leaf collimator further includes a guide rail box; the two leaf sets are disposed in the guide rail box, and configured to move in the guide rail box.

In some embodiments, the guide rail box includes a cover plate; the cover plate at least partially covers the upper end surface and/or the lower end surface of each leaf in the two leaf sets; the U-shaped optoelectronic switch system is disposed on an inner wall of the cover plate.

In some embodiments, the rail box includes a bracket disposed inside thereof; the U-shaped optoelectronic switch system is fixed by the bracket.

In some embodiments, the total length of a plurality of U-shaped optoelectronic switches corresponding to each leaf is not less than the length of the corresponding leaf.

In some embodiments, each of the drive devices is a motor.

In some embodiments, each of the drive devices includes a motor encoder disposed at a shaft end of the motor for measuring the rotation number of the motor.

In some embodiments, the multi-leaf collimator further includes a second processor; the second processor can obtain specific position information of the corresponding leaf according to the rotation number of the motor measured by the motor encoder.

In some embodiments, the multi-leaf collimator further includes a controller; the controller is configured to control the motion of the plurality of leaves according to processing results of the first processor and/or the second processor.

In another aspect, a driving method of the above multi-leaf collimator is provided, which comprises leaves moving in U-shaped grooves along a facing direction of two leaf sets under driving of corresponding driving devices; a U-shaped optoelectronic switch system generating pulse signals during motion of the leaves; and a first processor receiving and processing the pulse signals to obtain a quantized value of state of motion of each leaf.

In some embodiments, each drive device is a motor; each motor includes a motor encoder, arranged at a shaft end of the motor, for measuring a rotation number of the motor; the multi-leaf collimator further includes a second processor; the second processor can obtain specific position information of a corresponding leaf according to the rotation number of the motor measured by the motor encoder. The driving method further comprises the second processor processing the rotation number of the motor measured by the motor encoder to obtain the specific position information of the corresponding leaf.

In some embodiments, the multi-leaf collimator further includes a controller. The driving method further comprises the controller receiving processing results of the first processor and/or the second processor and controlling the motion of the plurality of leaves according to the processing results.

In yet another aspect, a radiotherapy device is provided, which comprises a treatment head emitting and directing a radiation beam and the above multi-leaf collimator for shaping the radiation beam.

DETAILED DESCRIPTION

The present disclosure will be further described in combination with the drawings and embodiments.

In one aspect, the present disclosure provides a multi-leaf collimator. The multi-leaf collimator includes two leaf sets disposed opposite to each other, a plurality of drive devices, a U-shaped optoelectronic switching system and a first processor.

Each leaf set includes a plurality of leaves, each of the leaves includes an upper end surface and a lower end surface opposite to each other, and a front end surface and a rear end surface opposite to each other. The front end surfaces of the leaves in the two leaf sets are facing each other. Each of the leaves is connected to a corresponding drive device, and each of the leaves may be configured to move along the facing direction (that is, the direction of the arrow in FIG. 1) of the two leaf sets under driving of the corresponding drive device. The U-shaped optoelectronic switch system includes one or more U-shaped optoelectronic switches, corresponding to each leaf, arranged in the motion direction of the leaf. The U-shaped optoelectronic switch(es) is disposed at a side of the upper end surface and/or a side of the lower end surface of the corresponding leaf. Each U-shaped optoelectronic switch includes a U-shaped groove, a transmitter located on a side of the U-shaped groove and a receiver located on the other opposite side of the U-shaped groove, and the corresponding leaf is disposed in the U-shaped groove. When the corresponding leaf is configured to move in the U-shaped groove along the facing direction of the two leaf sets, the U-shaped optoelectronic switch system generates pulse signals. The first processor is connected to the U-shaped optoelectronic switch system and configured to process pulse signals output by the U-shaped optoelectronic switch system to obtain a quantized value of the state of motion of each leaf.

Figure 1:
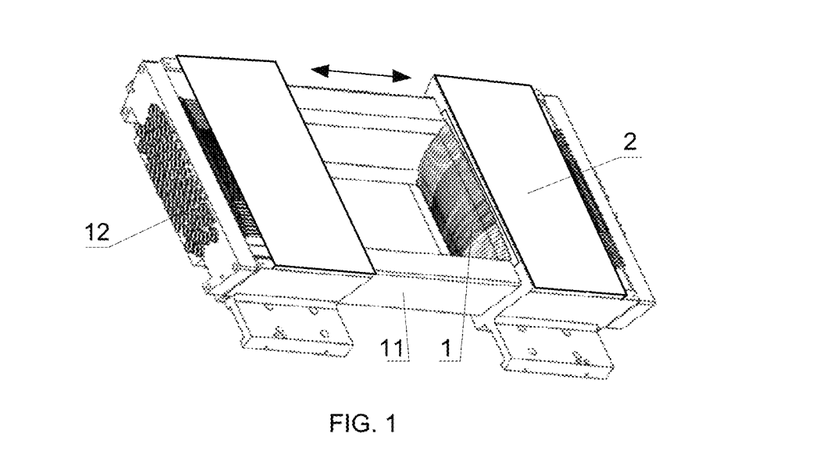
FIG. 1 is a schematic diagram of a structure of a multi-leaf collimator according to some embodiments of the present disclosure.

As shown in FIG. 1, each leaf set in the multi-leaf collimator includes a plurality of leaves 1 and a plurality of drive devices 12 for driving the plurality of leaves 1. The plurality of drive devices 12 drive the plurality of leaves 1 in one-to-one correspondence. The two leaf sets can relatively move by the drive of the plurality of drive devices 12. Each leaf 1 is connected to a corresponding drive device 12, and each leaf 1 can move under the drive of the corresponding drive device 12, that is, moving along the direction of the arrow in FIG. 1.

Figure 2A:
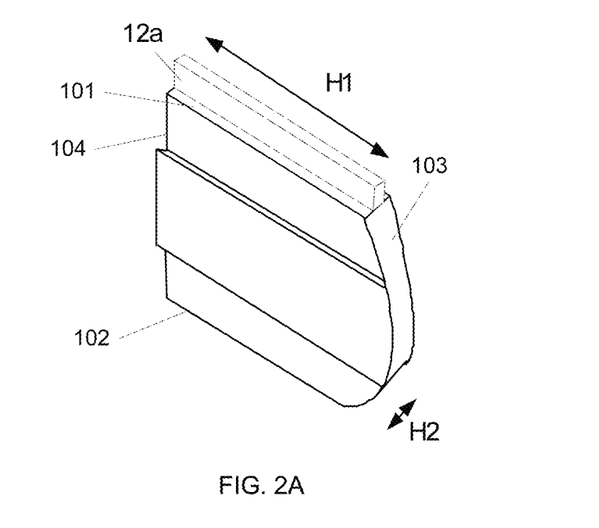
FIG. 2A is a schematic diagram of a structure of a leaf in a multi-leaf collimator according to some embodiments of the present disclosure.
Figure 2B:
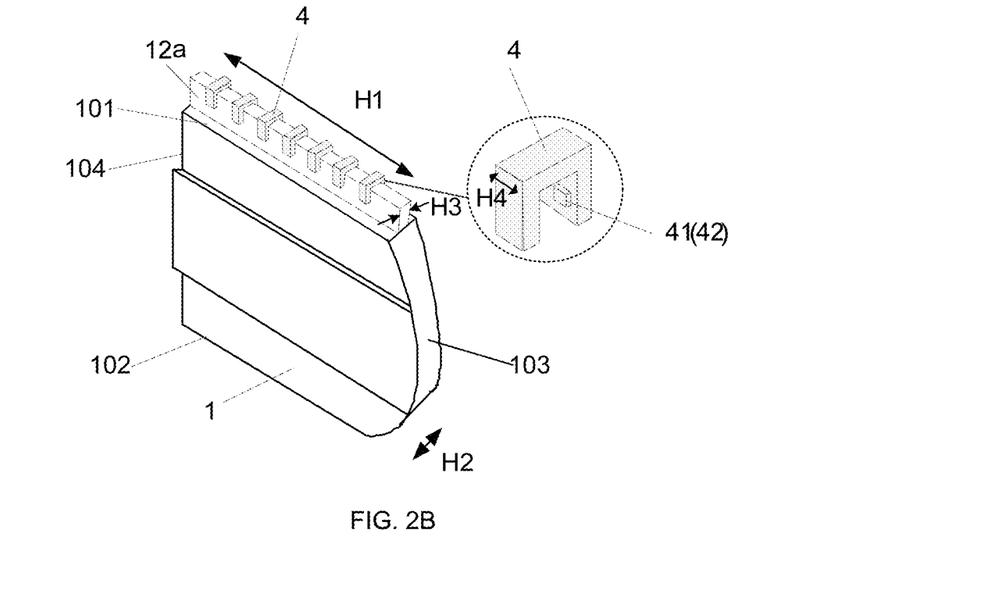
FIG. 2B is a schematic diagram of a cooperation of a leaf of a multi-leaf collimator and a U-shaped optoelectronic switch according to some embodiments of the present disclosure.
Figure 2C:
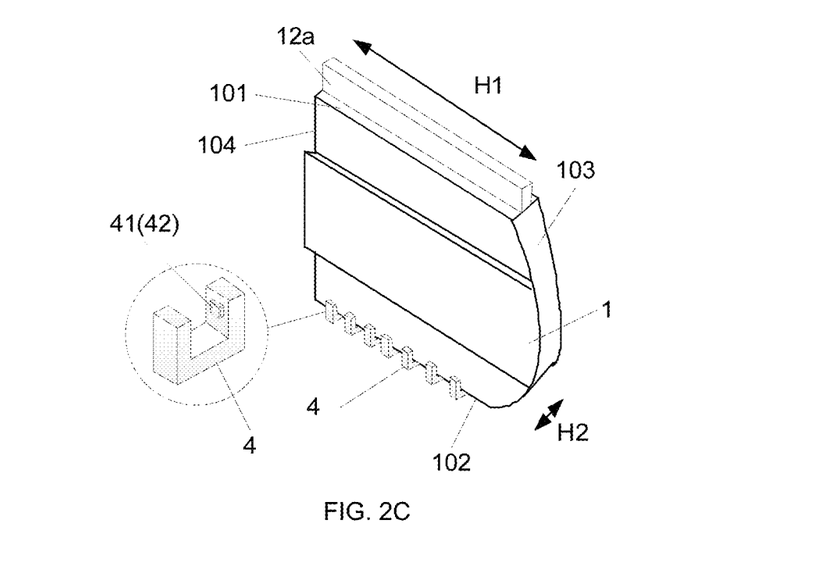
FIG. 2C is a schematic diagram of another cooperation of a leaf of a multi-leaf collimator and a U-shaped optoelectronic switch according to some embodiments of the present disclosure.

As shown in FIGS. 2A-2C, each leaf 1 includes an upper end surface 101 and a lower end surface 102 opposite to each other, and a front end surface 103 and a rear end surface 104 opposite to each other. The U-shaped optoelectronic switch system A11 includes one or more U-shaped optoelectronic switches 4 arranged corresponding to each leaf 1. The one or more U-shaped optoelectronic switches 4 are disposed at a side of the corresponding leaf 1 along the motion direction of the corresponding leaf 1. For example, FIG. 2B shows that a plurality of U-shaped optoelectronic switches 4 are disposed at a side of the upper end surface 101 of the leaf 1, and FIG. 2C shows that a plurality of U-shaped optoelectronic switches 4 are disposed at a side of the lower end surface 102 of the leaf 1. In some examples, a plurality of U-shaped optoelectronic switches 4 are disposed at the side of the upper end surface 101 and the side of the lower end surface 102 of the leaf 1. Each U-shaped optoelectronic switch 4 includes a U-shaped groove, a transmitter 41 and a receiver 42 located on two sides of the U-shaped groove (the transmitter 41 located on a side of the U-shaped groove, and the receiver 42 located on the other opposite side of the U-shaped groove). As shown in FIG. 2B and FIG. 2C, the leaf 1 is disposed in the U-shaped groove and can move in the U-shaped groove. When the leaf 1 moves, it passes through or leaves a certain U-shaped optoelectronic switch 4, so that the U-shaped optoelectronic switch 4 generates corresponding pulse signals. For example, taking a single U-shaped optoelectronic switch 4 as an example, when the leaf 1 is located in the U-shaped groove of the U-shaped optoelectronic switch 4, the leaf 1 blocks the transmitter 41 and the receiver 42 on two sides of the U-shaped groove, and the U-shaped optoelectronic switch 4 does not generate pulse signals; when the leaf 1 leaves the U-shaped groove of the U-shaped optoelectronic switch 4, the signal emitted by the transmitter 41 on one side of the U-shaped groove is received by the receiver 42 on the other opposite side of the U-shaped groove, thereby the U-shaped optoelectronic switch 4 generates pulse signals.

Figure 4:
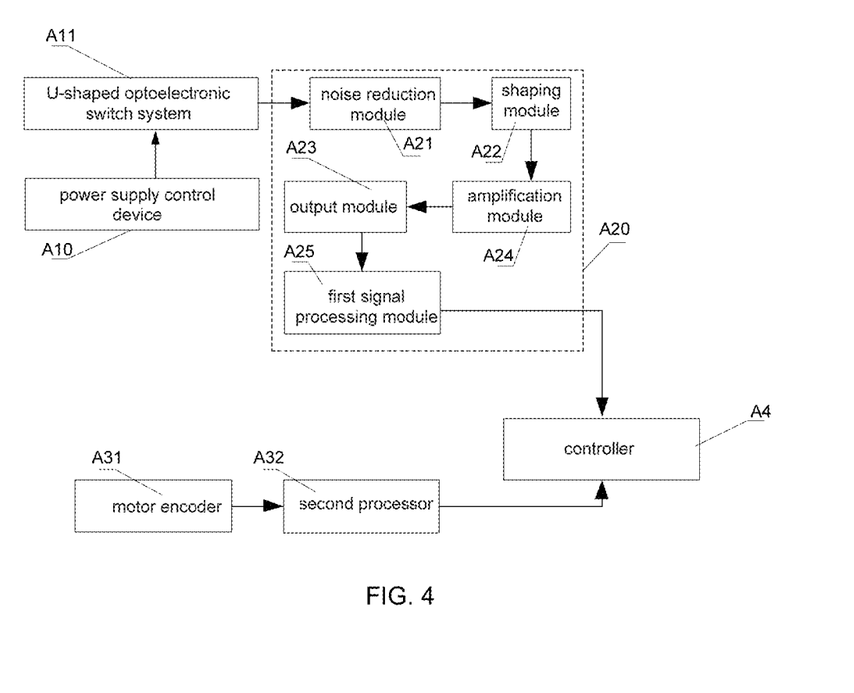
FIG. 4 is a schematic diagram of a control system of a multi-leaf collimator according to some embodiments of the present disclosure.

As shown in FIG. 4. The U-shaped optoelectronic switch system A11 is connected to the first processor A20. The first processor A20 is used to process pulse signals output by the U-shaped optoelectronic switch system A11 to obtain a quantized value of the state of motion of a leaf. Herein, the quantized value may be a signal mode or a digital mode, and may be a direct displacement or a relative displacement.

Taking the U-shaped optoelectronic switch 4 disposed at the same distance on the moving track of the leaf 1 as an example, when the leaf 1 moves, the U-shaped optoelectronic switch 4 can be alternately turned on and off to generate a series of pulse signals. The first processor A20 receives the pulse signals, and can determine the moving direction of the leaf 1 according to the phase of the first pulse generated by the U-shaped optoelectronic switch 4; when the leaf 1 moves from the initial position to a certain position, the first processor can determine the current position of the leaf 1 according to the U-shaped optoelectronic switch that does not generate pulse signals. In addition, the motion velocity of the leaf 1 can also be determined based on the time difference of a particular pulse front edge generated by the two adjacent U-shaped optoelectronic switches 4 during the motion.

In some embodiments, the side of the upper end surface and/or the side of the lower end surface of the leaf 1 is provided with a trigger structure; the trigger structure is located in the U-shaped groove and is configured to move with the leaf 1 in the U-shaped groove. For example, the trigger structure is a portion of the leaf 1 disposed at the side of the upper end surface of the leaf 1 for sequentially passing through or leaving the U-shaped optoelectronic switch when the leaf 1 moves. Or, a triggering structure is provided at the side of the upper end surface 101 of the leaf 1 and a triggering structure is also provided at the side of the lower end surface 102 of the leaf 1, the triggering structures are capable of sequentially passing through or leaving the U-shaped optoelectronic switch 4 when the leaf 1 moves.

As shown in FIG. 2B, the trigger structure may be a trigger portion 12a. The trigger portion 12a is disposed on the upper end surface of the leaf, an extending direction of which is consistent with the extending direction of the leaf 1, and the length H1 of which is equivalent to the length of the leaf 1. The width H3 of the trigger portion 12a is less than the width H2 of the leaf 1, and the trigger portion 12a can pass through the U-shaped groove of the U-shaped optoelectronic switch 4. It is also possible to make the central portion of the leaf 1 wider so that the side of the upper end surface or the side of the lower end surface of the leaf 1 can have a space for accommodating the U-shaped optoelectronic switch 4 and the tightness between the leaves 1 may be ensured. If the U-shaped optoelectronic switch 4 is disposed at the side of the lower end surface of the leaf 1, the corresponding structure may be adjusted in such a manner as to be provided at the side of the upper end surface.

In the embodiment, the trigger portion 12a can also be integrally formed with the leaf, which can be seen as a part of the leaf.

Figure 5:
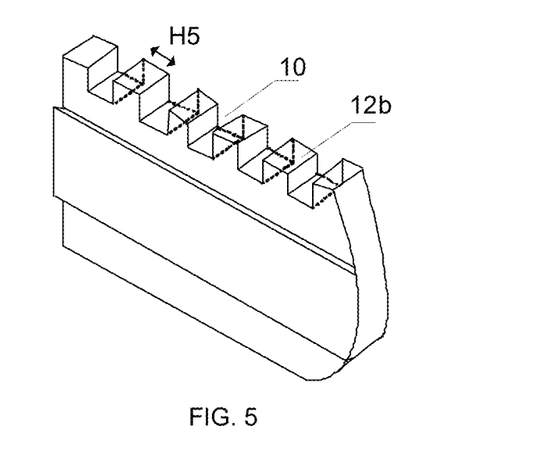
FIG. 5 is a schematic diagram of another structure of a leaf in a multi-leaf collimator according to some embodiments of the present disclosure.
Figure 6:
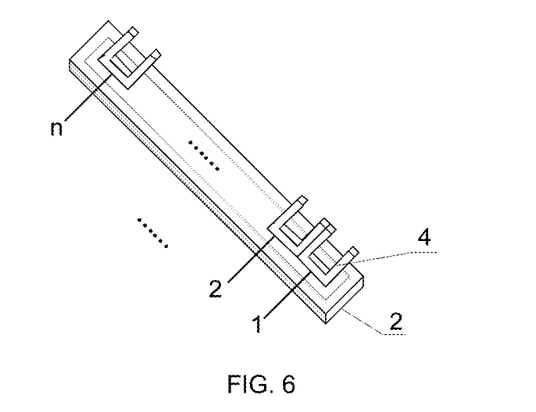
FIG. 6 is a schematic diagram of an arrangement of a layout diagram of U-shaped optoelectronic switches according to some embodiments of the present disclosure.

In some embodiment, the trigger structure may be a plurality of bosses 12b spaced from each other, disposed at the side of the upper end surface or the side of the lower end surface of the leaf. As shown in FIG. 5, the upper end surface of the leaf 1 is provided with a plurality of bosses 12b which are regularly arranged; the gaps between the bosses 12b are grooves 10. When the leaf 1 moves, the bosses 12b sequentially pass through the U-shaped optoelectronic switches 4 to cause the U-shaped optoelectronic switches 4 to be turned on or off to generate a series of pulse signals. Similarly, the state of motion of the leaf 1 can be determined according to the analysis of these pulse signals. Therefore, since the plurality of bosses 12b continuously disposed on the leaf 1 can make the U-shaped optoelectronic switches 4 continuously generate pulse signals, it is only needed to analyze one or several sets of pulse signals for each leaf 1, that is, each leaf 1 may be provided with fewer U-shaped optoelectronic switches 4.

In some embodiment, the bosses 12b on the upper end surface of the leaf 1 are disposed at equal distance, which facilitates analysis of the pulse signals and calculation of the state of motion of the leaf 1. In this case, one U-shaped optoelectronic switch 4 is disposed at the side of the upper end surface or the side of the lower end surface of each leaf 1.

In some embodiment, the distance between two adjacent bosses 12b is equal to the width H4 of the U-shaped optoelectronic switch 4, so that the bosses 12b passing through the U-shaped optoelectronic switches 4 can achieve good continuity, and generate uniform signals with a shorter period, thereby the accuracy of monitoring is higher. Of course, the width H5 of each boss may also be equal to the width H4 of the U-shaped optoelectronic switch 4.

In some embodiment, as shown in FIG. 1, the multi-leaf collimator includes a guide rail box 11. The two leaf sets are disposed in the guide rail box 11, and the plurality of leaves 1 in the two leaf sets move within the rail box 11. The guide rail box 11 is further provided with a cover plate 2 for partially covering the upper end surface or the lower end surface of each leaf 1.

In some embodiment, the U-shaped optoelectronic switches 4 can be disposed on the inner wall of the guide rail box 11 and disposed at the side of the upper end surface or the side of the lower end surface of the leaf 1. Specifically, the U-shaped optoelectronic switches 4 can be disposed on the inner wall of the cover plate 2 of the guide rail box 11.

In some embodiment, the rail box 11 includes a bracket disposed inside thereof, and the bracket is located on the side of the upper end surface or the side of the lower end surface of each leaf 1 in the two leaf sets. The U-shaped optoelectronic switch 4 can be positioned and fixed by a bracket provided in the rail box 11.

Figure 3:
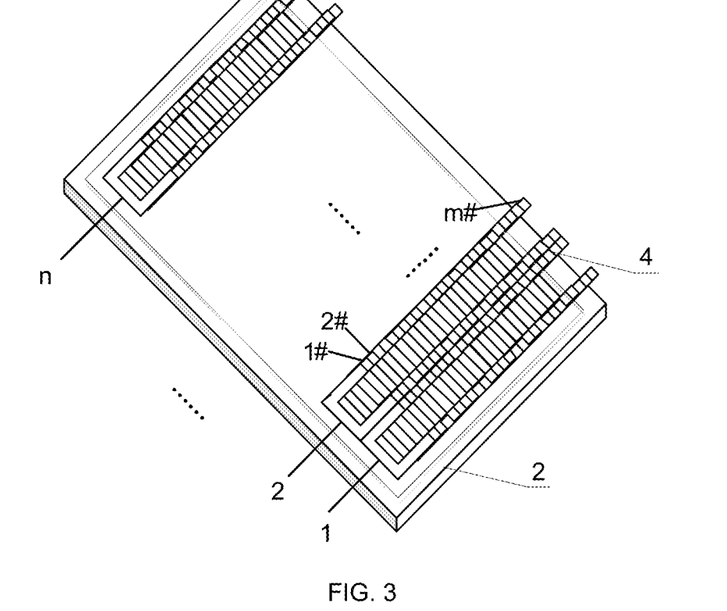
FIG. 3 is a schematic diagram of an arrangement of U-shaped optoelectronic switches according to some embodiments of the present disclosure.

In some embodiment, as shown in FIG. 3, each of the leaves is provided with a column of U-shaped optoelectronic switches 4, that is, the number of the leaves is the same as the number of columns of the U-shaped optoelectronic switches 4. These U-shaped optoelectronic switches 4 constitute the U-shaped optoelectronic switch system A11, and the total length of one column of U-shaped optoelectronic switches 4 of each leaf arranged along the motion direction of each leaf 1 is not less than the length of the corresponding leaf 1, which can ensure that the overall length of the leaf 1 is monitored properly. Each column of the U-shaped optoelectronic switches 4 is sequentially arranged adjacent to each other, or spaced from each other. For example, as shown in FIG. 3, each column of U-shaped optoelectronic switches 4 includes U-shaped optoelectronic switches arranged in turn from 1# to m#. The number of the U-shaped optoelectronic switches 4 in each column depends on the length of the leaf 1, for the distance between the U-shaped optoelectronic switches 4 in each column, the shorter the distance is, the more accurate the state of motion of the leaf 1 will be reflected.

In some embodiment, the first processor A20 includes: a noise reduction module A21 (for example, a filter circuit, a filter, etc.) for performing noise reduction processing on the switching signals of the U-shaped optoelectronic switch system, a shaping module A22 (for example, phase-shift circuit, etc.) for shaping the denoised signals, an amplification module A24 (for example, a transistor amplifier circuit, a field effect tube amplifier circuit, etc.) for amplifying the shaped signals, an output module A23 (for example, an output terminal, etc.) for outputting the amplified signals, and a first signal processing module A25 (for example, a Fast Fourier transform processor, a digital filer, a single chip digital signal processor, etc.) for processing the final output signals to obtain a quantized value of the state of motion of a leaf.

In some embodiment, the drive device 12 may be a motor or other drive structure, for example, a cylinder drive.

In some embodiment, taking the driving device 12 being motors as an example, a motor encoder A31 for measuring the rotation number of the motor is arranged at the shaft end of the motor. The rotation number of the motor can be measured by the motor encoder A31.

In some embodiment, the multi-leaf collimator further includes a second processor A32. The second processing module A32 can be used to calculate the motion displacement or specific position information of the leaf according to the rotation number of the motor. Or, the second processor A32 may calculate the motion displacement of the leaf according to the rotation number of the motor, and may also obtain the position information of the leaf according to the motion displacement and the original position of the leaf.

In some embodiment, the multi-leaf collimator further includes a controller A4. The controller A4 can determine and control the motion of the leaves according to processing results of the first processor A20, or determine and control the motion of the leaves according to processing results of the second processor A32. The controller A4 can more accurately determine and control the motion of the leaves in combination with the processing results of the first processor A20 and the second processor A32.

Thus, the monitoring of the leaves 1 is performed simultaneously by the motor encoder A31 and the U-shaped optoelectronic switch system A11. The motor encoder A31 uses the rotation number of motor to calculate the related information of motion of the leaves, which belongs to an indirect monitoring; and the monitoring of the U-shaped optoelectronic switch system A11 belongs to a direct monitoring to the leaves. Therefore, the motor encoder A31 and the U-shaped optoelectronic switch system A11 form a closed-loop monitoring to the leaves.

In some embodiment, referring to FIG. 4, the U-shaped optoelectronic switch system A11 is also connected to a power supply control device A10. The power supply control device A10 can be a device (such as a power supply box, a power supply, etc.) that can supply power to the U-shaped optoelectronic switch system A11. The power supply control device A10 is used for controlling the emission time of the U-shaped optoelectronic switches 4. For example, the driving device 12 of the leaf 1 acquires a driving signal, while the power supply control device A10 is provided with a control signal to turn on the U-shaped optoelectronic switches 4 to emit light when the leaf 1 starts moving or before the leaf 1 starts to move. As such, the energy consumed by the U-shaped optoelectronic switches can be reduced when the leaf 1 are not moving.

In some embodiment, the power supply control device A10 is used for controlling the emission duration of the U-shaped optoelectronic switches 4, for example, the leaf 1 stops moving, while the power supply control device A10 is provided with a control signal to turn off the U-shaped optoelectronic switches 4 when the leaf 1 stops moving or after the leaf 1 has stopped moving for a period of time, so that the energy consumed by the U-shaped optoelectronic switches can be reduced.

In another aspect, the present disclosure provides a driving method of a multi-leaf collimator, the driving method includes the leaves moving in the U-shaped groove along the facing direction of the two leaf sets under driving of the corresponding driving devices; generating pulse signals during the motion of the leaves by the U-shaped optoelectronic switch system; and the first processor receiving and processing the pulse signals to obtain a quantized value of the state of motion of each leaf.

When the leaf moves between the transmitter and the receiver of the U-shaped optoelectronic switch, the leaf blocks the signals emitted from the transmitter, thereby the receiver cannot receive the signals; when the leaf is not located between the transmitter and receiver of the U-shaped optoelectronic switch, the signals emitted from the transmitter can be received by the receiver. The U-shaped optoelectronic switch system is connected to the first processor; the first processor is used for processing pulse signals output by the U-shaped optoelectronic switch system (i.e. the transmitter and/or the receiver) to obtain quantized values of the state of motion of the leaves.

In some embodiment, the drive device in the above multi-leaf collimator is a motor or other drive structure, and the above multi-leaf collimator further includes a second processor. Each motor includes a motor encoder, arranged at the shaft end of the motor, for measuring the rotation number of the motor. The second processor can obtain the specific position information of the corresponding leaf according to the rotation number of the motor measured by the motor encoder. The driving method further includes the second processor processing the rotation number of the motor measured by the motor encoder to obtain the specific position information of the corresponding leaf.

In some embodiment, the above multi-leaf collimator further includes a controller. The driving method further includes the controller receiving the processing results of the first processor and/or the second processor and controlling the motion of the plurality of leaves according to the processing results.

In some embodiment, the U-shaped optoelectronic switch system A11 includes a small number of the U-shaped optoelectronic switches, thereby the material cost can be greatly reduced.

As shown in FIG. 5, the upper end surface of the leaf 1 is provided with a plurality of bosses 12b which are regularly arranged; the gaps between the bosses 12b are grooves 10. When the leaf 1 moves, the bosses 12b sequentially pass through the U-shaped optoelectronic switches 4 to cause the U-shaped optoelectronic switches 4 to be turned on or off to generate a series of pulse signals. Similarly, the state of motion of the leaf 1 can be determined according to the analysis of these pulse signals. Therefore, since the plurality of bosses 12b continuously disposed on the leaf 1 can make the U-shaped optoelectronic switches 4 continuously generate pulse signals, it is only needed to analyze one or several sets of pulse signals for each leaf, that is, each leaf may be provided with fewer U-shaped optoelectronic switches 4.

In some embodiment, only one U-shaped optoelectronic switch is disposed on the upper end surface or the lower end surface of each leaf 1; the bosses 12b on the upper end surface or the lower end surface of the leaf 1 are disposed at equal distance, so that it is convenient to analyze the pulse signals and calculate the state of motion of the leaf. The distance between two adjacent bosses 12b is equal to the width H4 of the U-shaped optoelectronic switch 4, so that the bosses 12b passing through the U-shaped optoelectronic switches 4 can achieve good continuity, and generate uniform signals with a shorter period, thereby the accuracy of monitoring is higher. Of course, the width H5 of each boss 12b may also be equal to the width H4 of the U-shaped optoelectronic switch 4.

For the positioning and fixing of the U-shaped optoelectronic switches, the processing of the signals, etc., reference may be made to the foregoing setting and processing manner, which will not be described herein again.

In another aspect, the present disclosure provides a radiotherapy device comprising a treatment head and the above described multi-leaf collimator. The treatment head is used to emit and direct a radiation beam; the multi-leaf collimator is used to shape the radiation beam; such that the radiation beam that illuminates the treatment area of a patient matches the shape of the tumor.

The above is a further detailed description of the present disclosure in combination with the specific preferred implementation manners, and it cannot be assumed that the specific implementations of the present disclosure are limited to these descriptions. For a person of ordinary skill in the field to which the present disclosure pertains, on the premise of not departing from the concept of the present disclosure, a number of simple deductions or substitutions may be made, which shall be considered as belonging to the protection scope of the present disclosure.

What is claimed is:
1. A multi-leaf collimator, comprising
two leaf sets disposed opposite to each other, wherein each leaf set includes a plurality of leaves, each of the leaves includes an upper end surface and a lower end surface opposite to each other, and a front end surface and a rear end surface opposite to each other, the front end surfaces of the leaves in the two leaf sets are facing each other;

a plurality of drive devices, wherein each of the leaves is connected to a corresponding drive device, and each of the leaves is configured to move along the facing direction of the two leaf sets under driving of the corresponding drive device;

a U-shaped optoelectronic switching system, wherein the U-shaped optoelectronic switching system includes one or more U-shaped optoelectronic switches, corresponding to each leaf, arranged in the motion direction of the leaf, the one or more U-shaped optoelectronic switch are disposed at a side of the upper end surface and/or a side of the lower end surface of a corresponding leaf; each U-shaped optoelectronic switch includes a U-shaped groove, a transmitter located at a side of the U-shaped groove and a receiver located at the other opposite side of the U-shaped groove; the corresponding leaf is disposed in the U-shaped groove, when the corresponding leaf is configured to move in the U-shaped groove along the facing direction of the two leaf sets, the U-shaped optoelectronic switch system generates pulse signals; and a first processor, wherein the first processor is connected to the U-shaped optoelectronic switch system and configured to process pulse signals output by the U-shaped optoelectronic switch system to obtain a quantized value of the state of motion of each leaf.

2. The multi-leaf collimator according to claim 1, wherein the upper end surface and/or the lower end surface of the leaf is provided with a trigger structure; the trigger structure is located in the U-shaped groove and is configured to move with the corresponding leaf in the U-shaped groove.

3. The multi-leaf collimator according to claim 2, wherein a width of the trigger structure is less than a width of the corresponding leaf.

4. The multi-leaf collimator according to claim 2, wherein the trigger structure includes a plurality of bosses spaced from each other.

5. The multi-leaf collimator according to claim 4, wherein a width of the boss and/or a distance between two adjacent bosses is equal to a width of the U-shaped optoelectronic switch.

6. The multi-leaf collimator according to claim 1, wherein a plurality of the U-shaped optoelectronic switches corresponding to each leaf are sequentially arranged adjacent to each other or spaced from each other.

7. The multi-leaf collimator according to claim 1, further comprising a guide rail box; the two leaf sets are disposed in the guide rail box, and configured to move in the guide rail box.

8. The multi-leaf collimator according to claim 7, wherein the guide rail box includes a cover plate; the cover plate at least partially covers the upper end surface and/or the lower end surface of each leaf in the two leaf sets; the U-shaped optoelectronic switch system is disposed on an inner wall of the cover plate.

9. The multi-leaf collimator according to claim 7, wherein the rail box includes a bracket disposed inside thereof; the U-shaped optoelectronic switch system is fixed by the bracket.

10. The multi-leaf collimator according to claim 1, wherein the total length of a plurality of U-shaped optoelectronic switches corresponding to each leaf is not less than the length of the corresponding leaf.

11. The multi-leaf collimator according to claim 1, wherein each of the drive devices is a motor.

12. The multi-leaf collimator according to claim 11, wherein each of the drive devices includes a motor encoder disposed at a shaft end of the motor for measuring the rotation number of the motor.

13. The multi-leaf collimator according to claim 12, further comprising a second processor, wherein the second processor can obtain specific position information of the corresponding leaf according to the rotation number of the motor measured by the motor encoder.

14. The multi-leaf collimator according to claim 13, further comprising a controller, wherein the controller is configured to control the motion of the plurality of leaves according to processing results of the first processor and/or the second processor.

15. A radiotherapy device, comprising a treatment head emitting and directing a radiation beam, and a multi-leaf collimator for shaping the radiation beam;

wherein the multi-leaf collimator comprises two leaf sets disposed opposite to each other, wherein each leaf set includes a plurality of leaves, each of the leaves includes an upper end surface and a lower end surface opposite to each other, and a front end surface and a rear end surface opposite to each other, the front end surfaces of the leaves in the two leaf sets are facing each other;

a plurality of drive devices, wherein each of the leaves is connected to a corresponding drive device, and each of the leaves is configured to move along the facing direction of the two leaf sets under driving of the corresponding drive device;

a U-shaped optoelectronic switching system, wherein the U-shaped optoelectronic switching system includes one or more U-shaped optoelectronic switches, corresponding to each leaf, arranged in the motion direction of the leaf, the one or more U-shaped optoelectronic switch are disposed at a side of the upper end surface and/or a side of the lower end surface of a corresponding leaf, each U-shaped optoelectronic switch includes a U-shaped groove, a transmitter located at a side of the U-shaped groove and a receiver located at the other opposite side of the U-shaped groove; the corresponding leaf is disposed in the U-shaped groove, when the corresponding leaf is configured to move in the U-shaped groove along the facing direction of the two leaf sets, the U-shaped optoelectronic switch system generates pulse signals; and a first processor, wherein the first processor is connected to the U-shaped optoelectronic switch system and configured to process pulse signals output by the U-shaped optoelectronic switch system to obtain a quantized value of the state of motion of each leaf.

* * * * *